(12) United States Patent
Lozano

(10) Patent No.: US 8,849,392 B2
(45) Date of Patent: Sep. 30, 2014

(54) IDENTIFYING AREAS OF THE BRAIN BY EXAMINING THE NEURONAL SIGNALS

(71) Applicant: Andres M Lozano, Toronto (CA)

(72) Inventor: Andres M Lozano, Toronto (CA)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

(21) Appl. No.: 13/632,522

(22) Filed: Oct. 1, 2012

(65) Prior Publication Data

US 2013/0172716 A1 Jul. 4, 2013

Related U.S. Application Data

(63) Continuation of application No. 11/928,536, filed on Oct. 30, 2007, now Pat. No. 8,280,514.

(60) Provisional application No. 60/855,532, filed on Oct. 31, 2006.

(51) Int. Cl.
*A61B 5/04* (2006.01)
*A61B 5/00* (2006.01)
*A61N 1/05* (2006.01)
*A61B 5/0478* (2006.01)
*A61B 5/048* (2006.01)
*A61N 1/36* (2006.01)

(52) U.S. Cl.
CPC ......... *A61B 5/04001* (2013.01); *A61B 5/4064* (2013.01); *A61N 1/0534* (2013.01); *A61B 5/0478* (2013.01); *A61B 5/048* (2013.01); *A61B 5/6864* (2013.01); *A61N 1/0529* (2013.01); *A61N 1/36082* (2013.01); *A61B 5/0031* (2013.01)

USPC .......................................................... 600/544

(58) Field of Classification Search
USPC .................................... 607/45; 600/544
See application file for complete search history.

(56) References Cited

U.S. PATENT DOCUMENTS

| | | | |
|---|---|---|---|
| 3,731,681 A | 5/1973 | Blackshear et al. | |
| 3,951,147 A | 4/1976 | Tucker et al. | |
| 4,692,147 A | 9/1987 | Duggan | |
| 4,772,263 A | 9/1988 | Dorman et al. | |
| 5,423,877 A | 6/1995 | Mackey | |
| 5,752,911 A | 5/1998 | Canedo et al. | |
| 5,840,069 A | 11/1998 | Robinson | |
| 6,036,459 A | 3/2000 | Robinson | |
| 6,132,361 A | 10/2000 | Epstein et al. | |
| 6,176,242 B1 | 1/2001 | Rise | |
| 6,356,784 B1 * | 3/2002 | Lozano et al. | 607/2 |

(Continued)

OTHER PUBLICATIONS

Kuhn et al. The relationship between local field potential and neuronal discharge in the subthalamic nucleus of patients with Parkinson's disease. Exp Neurol. Jul. 2005;194(1):212-20.*

(Continued)

*Primary Examiner* — Christopher D Koharski
*Assistant Examiner* — Jeremiah Kimball

(57) ABSTRACT

The present invention relates to a method of identifying a region of the brain by measuring neuronal firing and/or local field potentials by recording discharges from at least one implanted electrode and analyzing the recording of the discharges within the beta frequency band range to determine an area of beta oscillatory activity. Once the region of the brain is identified, this region may be stimulated to disrupt the beta oscillatory activity thereby treating a movement disorder.

9 Claims, 7 Drawing Sheets

(56) References Cited

U.S. PATENT DOCUMENTS

| | | | |
|---|---|---|---|
| 6,425,852 B1 | 7/2002 | Epstein et al. | |
| 6,567,699 B2 | 5/2003 | Alferness et al. | |
| 6,592,509 B1 | 7/2003 | Hunter, Jr. | |
| 6,620,151 B2 | 9/2003 | Blsichak et al. | |
| 6,666,845 B2 | 12/2003 | Hooper et al. | |
| 7,151,961 B1* | 12/2006 | Whitehurst et al. | 607/2 |
| 2004/0153129 A1 | 8/2004 | Pless et al. | |
| 2005/0027284 A1 | 2/2005 | Lozano et al. | |
| 2005/0125043 A1 | 6/2005 | Tass et al. | |
| 2005/0149157 A1* | 7/2005 | Hunter et al. | 607/119 |
| 2005/0154424 A1 | 7/2005 | Tass et al. | |
| 2005/0277995 A1* | 12/2005 | Gill | 607/45 |
| 2006/0009815 A1* | 1/2006 | Boveja et al. | 607/45 |
| 2006/0047324 A1 | 3/2006 | Tass | |
| 2006/0212089 A1 | 9/2006 | Tass | |
| 2006/0276853 A1 | 12/2006 | Tass et al. | |
| 2007/0135860 A1 | 6/2007 | Tass | |
| 2007/0203532 A1 | 8/2007 | Tass et al. | |
| 2007/0225674 A1 | 9/2007 | Molnar et al. | |
| 2008/0269836 A1 | 10/2008 | Foffani et al. | |

OTHER PUBLICATIONS

Herzog et al. Most Effective Stimulation Site in Subthalamic Deep Brain Stimulation for Parkinson's Disease. Movement Disorders. vol. 19, No. 9, pp. 1050-1099 (2004).*
Brown et al. Effects of Stimulation of the Subthalamic Area on Oscillatory Pallidal Activity in Parkinson's Disease. Experimental Neurology, 188 (2004):480-490.*
Dostrovsky et al. Mechanisms of Deep Brain Stimulation. Movement Disorders, vol. 17, Suppl. 3 (2002):S63-S68.*
Limousin et al. Electrical Stimulation of the Subthalamic Nucleus in Advanced Parkinson's Disease. N Engl J Med, vol. 339, No. 16 (1998):1105-1111.*
Chen et al. Intra-operative recordings of local field potentials can help localize the subthalamic nucleus in Parkinson's disease surgery. Experimental Neurology. 198 (2006):214-221.*
Wingeier et al. Intra-operative STN DBS attenuates the prominent beta rhythm in the STN in Parkinson's disease. Experimental Neurology. 197 (2006):244-251.*
Weinberger et al. Beta Oscillatory Activity in the Subthalamic Nucleus and Its Relation to Dopaminergic Response in Parkinson's Disease. J Neurophysiol. 96 (2006):3248-3256.*
Bevan, et al., "Move to the rhythm: oscillations in the subthalamic nucleus-external globus pallidus network," Trends Neurosci 25:525-531, (2002).
Brown et al. Effects of Stimulation of the Subthalamic Area on Oscillatory Pallidal Activity in Parkinson's Disease. Experimental Neurology. 188 (2004):480-490.
Brown et al. Effects of Stimulation of the Subthalamic Area on Oscillatory Pallidal Activity in Parkinson's Disease. Experimental Neurology. 188 (2004):480-490.
Cassidy M, et al., "Movement-related changes in synchronization in the human basal ganglia," Brain 125:1235-1246, (2002).
Dostrovsky et al. Mechanisms of Deep Brain Stimulation. Movement Disorders. vol. 17, Suppl. 3 (2002):S63-S68.
Doyle LM, et al., "Levodopa-induced modulation of subthalamic beta oscillations during self-paced movements in patients with Parkinson's disease," Eur J Neurosci 21:1403-1412, (2005).
Herzog et al. "Most Effective Stimulation Site in Subthalamic Deep Brain Stimulation for Parkinson's Disease." Movement Disorders. (2004) vol. 19, No. 9, pp. 1050-1099.
Hutchison WD, et al., "Neurophysiological identification of the subthalamic nucleus in surgery for Parkinson's disease," Ann Neurol 44:622-628, (1998).
Kuhn AA, et al., "Event-related beta desynchronization in human subthalamic nucleus correlates with motor performance," Brain 127:735-746, (2004).

Kuhn, et al., "The relationship between local field potential and neuronal discharge in the subthalamic nucleus of patients with Parkinson's disease," Exp Neurol 194:212-220, (2005).
Levy R, et al., "Dependence of subthalamic nucleus oscillations on movement and dopamine in Parkinson's disease," Brain 125:1196-1209, (2002).
Levy R, et al., "High-frequency synchronization of neuronal activity in the subthalamic nucleus of parkinsonian patients with limb tremor," J Neurosci 20:7766-7775, (2000).
Limousin et al. Electrical Stimulation of the Subthalamic Nucleus in Advanced Parkinson's Disease. N Engl J Med. vol. 339, No. 16 (1998):1105-1111.
Lozano AM, et al., "Deep brain stimulation for Parkinson's disease: disrupting the disruption," Lancet Neurol 1:225-231, (2002).
Magill PJ, et al., "Synchronous unit activity and local field potentials evoked in the subthalamic nucleus by cortical stimulation," J Neurophysiol 92:700-714, (2004).
Marsden JF, et al., "Subthalamic nucleus, sensorimotor cortex and muscle interrelationships in Parkinson's disease," Brain 124:378-388, (2001).
Nini A, et al., "Neurons in the globus pallidus do not show correlated activity in the normal monkey, but phase-locked oscillations appear in the MPTP model of parkinsonism," J Neurophysiol 74:1800-1805, (1995).
Sharott A, et al., "Dopamine depletion increases the power and coherence of beta-oscillations in the cerebral cortex and subthalamic nucleus of the awake rat," Eur J Neurosci 21:1413-1422, (2005).
Tass, Peter A, "A model of desynchronizing deep brain stimulation with a demand-controlled coordinated reset of neural subpopulations," Biological Cybernetics, 89, 81-88 (2003).
Tass, Peter A, "Desynchronization of brain rhythms with soft phase-resetting techniques," Biological Cybernetics 87, 102-115 (2002).
Tass, Peter A, "Desynchronizing double-pulse resetting and application to deep brain stimulation," Biological Cybernetics 85, 343-354 (2001).
Tass, Peter A, "Effective desynchronization with bipolar double-pulse stimulation," Physical Review E 66, 036226 (2002).
Tass, Peter A, "Phase Resetting in Medicine and Biology: Stochastic Modelling and Data Analysis,", Chapter 10, 265-274, Springer-Verlag erlin Heidelbert, Germany, 1999.
Tass, Peter A, "Stochastic phase resetting of stimulus-locked responses of two coupled oscillators: Transient response clustering, synchronization,and desynchronization," Chaos, vol. 13, No. 1, Mar. 2003.
Tass, Peter A, "Stochastic Phase Resetting: A Theory for Deep Brain Stimulation," Progress of Theoretical Physics Supplement No. 139, 2000.
Tass, Peter A, et al., "Detection of n;m Phase Locking from Noisy Data: Application to Magnetoencephalography,"Physical Review Letters, vol. 81, No. 15, Oct. 12, 1998.
Tass, Peter A, et al., "Obsessive-Compulsive Disorder: Development of Demand-Controlled Deep Brain Stimulation with Methods from Stochastic Phase Resetting," Neuropsychopharmacology 28, S-27-S34 (2003).
Weinberger, Moran, et al., "Beta Oscillatory Activity in the Subthalmic Nucleus and its Relation to Dopaminergic Response in Parkinson's Disease," J. Neurophysiol. Dec. 2006; 96(6):3248-56.
Willams, et al., "Dopamine-dependent changes in the functional connectivity between basal ganglia and cerebral cortex in humans," Brain 125:1558-1569 (2002).
Williams, et al., "Behavioural cues are associated with modulations of synchronous oscillations in the human subthalamic nucleus," Brain 126:1975-1985 (2003).
Wingeier B, et al., "Intra-operative STN DBS attenuates the prominent beta rhythm in the STN in Parkinson's disease," Exp Neurol., (2006); 197(1):244-51, Epub Nov. 10, 2005.

* cited by examiner

IDENTIFYING AREAS OF THE BRAIN BY EXAMINING THE NEURONAL SIGNALS

CROSS-REFERENCE TO RELATED APPLICATIONS

This application is a continuation of U.S. application Ser. No. 11/928,536, filed Oct. 30, 2007, now U.S. Pat. No. 8,280,514, which claims the benefit of U.S. Provisional Application No. 60/855,532, filed Oct. 31, 2006, the disclosures of which are fully incorporated herein by reference for all purposes.

BACKGROUND

The present application is related to the fields of neurology and medicine and, more specifically, to identifying a specific region of the brain for therapeutic purpose (electrical simulation) in individuals with neurological disease, such as Parkinson's Disease.

In patients with neurological or psychiatric pathologies like, for example Parkinson's disease, nerve cell groups in circumscribed regions of the brain, for example the thalamus and the basal ganglia, are pathologically active, for example excessively synchronous. In these cases a large number of neurons synchronously generate action potentials. In healthy patients, the neurons in these regions of the brain fire qualitatively differently, for example, in an uncorrelated manner.

Recent studies suggest that beta (about 15-30 Hz) oscillatory activity in the subthalamic nucleus (STN) is greatly increased in Parkinson's Disease (PD) patients and may interfere with movement execution (Cassidy et al., 2002; Levy et al., 2002; Kuhn et al., 2004; 2005; Williams et al., 2003; 2005). Dopaminergic medications decrease beta activity (Levy et al., 2002) and deep brain stimulation (DBS) in the STN may alleviate PD symptoms by disrupting this oscillatory activity. Depth recordings in PD patients have demonstrated beta oscillatory local field potential (LFP) activity in STN (Levy et al., 2002; Kuhn et al., 2005). Beta oscillatory LFP activity in the STN has been shown to be coherent with cortical EEG and contralateral EMG (Williams et al., 2002; Marsden et al., 2001).

BRIEF SUMMARY OF THE INVENTION

One embodiment of the present invention relates to a method of identifying a region of the brain by measuring neuronal firing and/or local field potentials by recording discharges from at least one implanted electrode and analyzing the recording of the discharges within the beta frequency band range to determine an area of beta oscillatory activity. The beta oscillatory activity can also be synchronized.

Another embodiment comprises a method of improving at least one symptom in an individual suspected of having a movement disorder, comprising the steps of: measuring neuronal firing and/or local field potentials by recording discharges from at least one electrode implanted in the subthalamic nucleus; analyzing the recording of the discharges within the beta frequency band range to determine an area of synchronized beta oscillatory activity; and stimulating the area to disrupt the beta oscillatory activity, thereby improving at least one symptom in the individual.

Yet further, another method of the present invention comprises a method of improving at least one symptom in an individual having a movement disorder, comprising the step of stimulating the dorsal subthalamic nucleus (STN) in the individual.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying figures. Figures provided herein are intended to help illustrate the invention or assist with developing an understanding of the invention, and are not intended to be definitions of the invention's scope.

DETAILED DESCRIPTION

I. Definitions

Figure 1A:
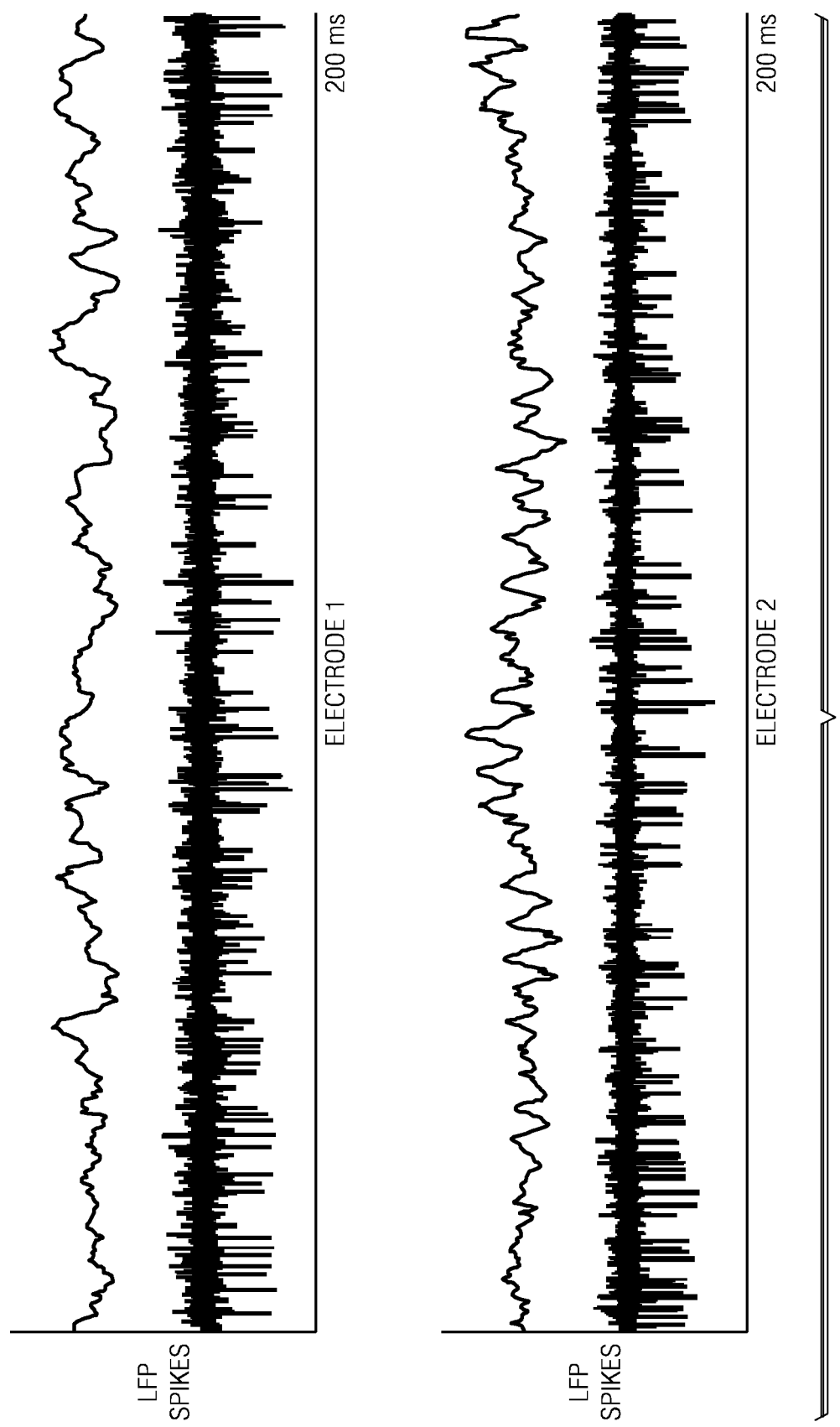
FIGS. 1A and 1B show examples of synchronized neuronal and LFP beta oscillatory activity (from one patient, right STN).

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method or composition described herein can be implemented with respect to any other method or composition described herein.

As used herein the term "local field potential" or "LFPs" refer to a particular class of electrophysiological signals, which are related to the sum of all neuronal activity within a volume of tissue.

As used herein the term "modulate" refers to the ability to regulate positively or negatively neuronal activity. Thus, the term modulate can be used to refer to increasing, decreasing, masking, altering, overriding or restoring neuronal activity.

As used herein, the term "movement disorder" refers to neurological conditions in which the major clinical expressions involve reduced normal movements or excessive or abnormal involuntary movements of the limbs, face or trunk.

As used herein, the term "neuronal" refers to a neuron which is a morphologic and functional unit of the brain, spinal column, and peripheral nerves.

As used herein, the term "neuron" refers to one of the cells that constitute nervous tissue, that have the property of transmitting and receiving nervous impulses, and that are composed of somewhat reddish or grayish protoplasm with a large nucleus containing a conspicuous nucleolus, irregular cytoplasmic granules, and cytoplasmic processes which are highly differentiated frequently as multiple dendrites or usually as solitary axons and which conduct impulses toward and away from the nerve cell body—called also nerve cell.

As used herein, the term "nerve" refers to any of the filamentous bands of nervous tissue that connect parts of the nervous system with the other organs, conduct nervous impulses, and are made up of axons and dendrites together with protective and supportive structures and that for the larger nerves have the fibers gathered into funiculi surrounded by a perineurium and the funiculi enclosed in a common epineurium.

As used herein, the term "stimulate" or "stimulation" refers to electrical stimulation that modulates the predetermined sites in the brain.

As used herein, the term "treating" and "treatment" refers to modulating certain areas of the brain so that the subject has an improvement in the disease, for example, beneficial or desired clinical results. For purposes of this application, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

Introduction

Through clinical research, Applicants have demonstrated that there is relationship between oscillatory activity of the LFP and neuronal spike discharges within the beta frequency band in PD patients. It is believed that the specific cells that exhibit the oscillatory relationship within the STN are the neuronal cells that mediate the pathological symptoms associated with PD. Accordingly, electrical stimulation of these specific cells interrupts the propagation of pathological signals through STN and thereby eliminates or mitigates the pathological symptoms of PD. By targeting these specific cells, electrical stimulation or other modulation (e.g., chemical modulation, magnetic modulation, heat modulation, etc.) is believed to lead to optimal therapeutic results with minimal side effects.

In one representative embodiment, the relationship between the phase of LFP beta oscillations and the phase of neuronal beta oscillations is utilized to position the electrodes of a stimulation lead during a DBS implantation procedure. Specifically, as the electrodes are traversed through an implantation track, the electrodes are utilized to detect LFP activity and neuronal spike activity within the beta frequency band. A suitable signal processing technique is applied to determine the phase relationship between the LFP and neuronal beta oscillations. If the respective phases of the two signals are sufficiently correlated at a specific position, the correct location for application of stimulation pulses for PD therapy has been reached. The positioning of the lead and, hence, the electrodes of the lead can then be fixed using suitable burr hole cap functionality. Because a relatively exact identification of the neuronal cells exhibiting pathological activity is possible, superior therapeutic results can be expected. For example, lower amplitude pulses can be applied which can lead to a lower degree of side effects and possibly lead to a longer duration of effectiveness of the therapy.

In another representative embodiment, the relationship between the phase of LFP beta oscillations and the phase of neuronal beta oscillations is utilized to control the application of stimulation pulses according to a closed-loop system. Specifically, it is believed that electrical stimulation need not be applied in a continuous manner for PD patients. Only when sufficient correlation between the phase of LFP beta oscillations and the phase of neuronal beta oscillations is detected, electrical stimulation is applied for some embodiments. Because electrical stimulation for PD is typically relatively high frequency, ceasing stimulation when stimulation is not necessary to control PD symptoms can conserve a significant amount of energy. Accordingly, an implanted stimulation system can operate for longer periods utilizing a closed-loop system according to some representative embodiments.

Clinical Research

The following examples are offered by way of example, and are not intended to limit the scope of the invention in any manner.

Patient Selection

Fourteen patients with advanced Parkinson's disease (PD) were treated with stereotactic surgery for implantation of subthalamic nucleus (STN) deep brain stimulation (DBS) electrodes. The group consisted of five females and nine males who, at the time of operation, had a mean age of 57 years (range 46-68). All patients were assessed preoperatively using the Unified Parkinson's Disease Rating Scale (UPDRS) before and after L-dopa intake. During surgery the patients were awake and "off" dopaminergic medications, at least 12 hours from the last oral dose of antiparkinsonian medications. Demographic details of the patients are given in Table 1.

TABLE 1

Summary of patients' details

| Case | Age (years) and sex | Disease duration (years) | Motor UPDRS on/off drugs pre-op | Power band used (Hz) |
|---|---|---|---|---|
| 1 | 60 F | 21 | 31/61.5 | R STN 11-21 Hz |
| 2 | 51 M | 10 | 13/50.5 | L STN 22-32 Hz |
| 3 | 61 M | N/A | 10.5/30.5 | L STN 15-25 Hz |
| 4 | 52 F | 19 | 15/68 | L STN 22-32 Hz |
| 5 | 56 F | N/A | 24/65 | R STN 25-35 Hz |
|   |   |   |   | L STN 25-35 Hz |
| 6 | 68 M | N/A | 33/46 | R STN 20-30 Hz |
| 7 | 57 M | 17 | 13/49 | R STN 20-30 Hz |
|   |   |   |   | L STN 24-34 Hz |
| 8 | 65 M | 21 | 22.5/41 | R STN 25-35 Hz |
|   |   |   |   | L STN 15-25 Hz |
| 9 | 49 M | 14 | 32.5/59 | R STN 24-34 Hz |
|   |   |   |   | L STN 24-34 Hz |
| 10 | 46 M | 9 | 15.5/58 | L STN 20-30 Hz |
| 11 | 50 M | 6 | 31/38.5 | R STN 20-30 Hz |
| 12 | 57 F | 15 | 9/31 | R STN 20-30 Hz |
|   |   |   |   | L STN 20-30 Hz |
| 13 | 63 F | 20 | 16/37.5 | R STN 23-33 Hz |
|   |   |   |   | L STN 23-33 Hz |
| 14 | 54 M | N/A | 8.5/32 | R STN 20-30 Hz |
|   |   |   |   | L STN 20-30 Hz |

Recordings

All recordings were performed in the resting state and under local anesthesia. Patients were not asked to perform any task, and epochs with movements were excluded. Physiological data was recorded simultaneously from two independently driven, microelectrodes (~25 μm tip length, 600 μm apart, ~0.2 MΩ impedance) during the electrophysiology mapping procedure. The localization procedure of the STN using microelectrode recording is described in detail (Hutchison et al., 1998). Briefly, the dorsal border of STN was noted by increase in background activity and high frequency neuronal discharge, the electrodes were advanced passed the ventral border of STN, at which point background noise usually decreases until the electrode reaches the substantia nigra pars reticulata, which was identified by higher frequency, lower amplitude discharges compared with STN.

All recordings are amplified 5000 times, filtered at 1 to 5000 Hz using the Guideline System GS3000 (Axon Instruments, Foster City, Calif.). The signals were acquired and digitized at 10 kHz using the commercially available device CED 1401 by Cambridge Electronic Designs (Cambridge, UK). Also, the linear distance between electrode tips was 0.83±0.3 mm (mean±SD, n=195).

The use of two microelectrodes was selected to enable the identification of coherent neuronal spike activity by respective pairs of neuronal cells. The identified coherent neuronal spike activity was then correlated to LFP beta oscillations as discussed below.

Data Analysis

Recordings from 21 sides in 14 patients were analyzed. In 7 patients both right and left sides were analyzed, only left STN recordings were analyzed in 4 patients and right STN in 3 patients. Only data of ≥17 seconds duration and without unexpected movements (based on EMG recordings and observations) or other artifacts were analyzed. Recording depths were realigned to the top of STN in each track, where 0 is the dorsal border of STN and negative values are ventral to the border.

The physiological data from these recordings was processed using the specialized tools in the Spike2™ product (Cambridge Electronic Design, Cambridge, UK). Specifically, the physiological data was subjected to various signal processing algorithms to identify spike times in the physiological data and to obtain unfiltered LFP data. Spike times can be detected using threshold crossings and waveform shape template matching. Unfiltered LFP data can be obtained utilizing a suitable "leaky integrator" (window averaging or a median filter). Spike times and unfiltered LFP data were then imported into MATLAB™ (version 6.5, The Math Works, Natick, Mass.) for further analysis.

The main statistical tool in MATLAB for data analysis was the discrete Fourier transform and its derivations calculated according to Halliday et al., (1995). After signals were downsampled to 1 kHz, spectra of LFP power were estimated by dividing the waveform signal into a number of sections of equal duration of 1.024 s (1024 data points, 512 point overlap), each section was windowed (Hanning window) and the magnitudes of the 1024 discrete Fourier transform of each section were squared and averaged to form the power spectrum, yielding a frequency resolution of 0.97 Hz. The power was transformed to a logarithmic scale and shown in decibels (dB).

To estimate the relative beta power according to distance, the frequency of the beta peak of each STN trajectory was identified, and the mean power across a 10 Hz window centered on the peak frequency was calculated at each recording site. LFP power at each recording site was then expressed as the percentage of the maximum power observed in the trajectory. Percentages of maximum power were averaged across subjects to give mean percentage of LFP beta power (Kuhn et al., 2005).

For spectral analysis of neuronal discharge, the statistical significance of spectral peaks was estimated using bootstrapping. The expected power spectrum was calculated by shuffling the observed inter-spike-intervals (ISIs) in order to disrupt the temporal patterning of the ISIs, giving an expected spectrum resulting from the ISI distribution. Subtraction of the expected spectrum from the observed spectrum resulted in a corrected spectrum. Relative beta power for the neuronal discharge spectrum according to distance was estimated from the original power spectrum in the same manner described above for estimating LFP power changes.

Coherence and cross-correlation analyses (Halliday et al., 1995; Rosenberg et al., 1989) were used to assess the relationship between simultaneously recorded data from separate electrodes, and between LFP and spike data recorded from the same microelectrode. Correlation histograms of the 11-35 Hz band pass filtered LFP were plotted for delays of 500 ms (1 ms bin width).

Changes in LFP power were evaluated by change-point analysis and control limits (Change-Point Analyzer 2.0 shareware program; Taylor Enterprises, Illinois). Change-point analysis iteratively uses a combination of cumulative sum (cusum) and bootstrapping to detect changes, and is more sensitive to change than control limits which based on plots of serial deviations from the mean (Taylor, 2000). Cusums were determined by plotting the sequentially summed deviation from the averaged power. The application of this technique to power changes in the basal ganglia has been used in previous studies (Williams et al., 2003; Kuhn et al., 2004). To examine the relationship between incidence of oscillatory cells and clinical motor symptoms and effectiveness of medications, part III (motor) UPDRS "on" and "off" total scores were used as well as subscores as evaluated 8.1±2.1 days (mean±SE) before surgery. The effectiveness of the antiparkinsonian medications was calculated as the difference between the "on" and "off" scores, divided by the "off" score to give the percentage of benefit. Non-linear regression statistics were used to better describe the correlations.

Results

Coherence Between Neuronal and LFP Beta Oscillatory Activity in the STN

Of 200 single and multiunit recordings in 14 patients, 56 (28%) displayed significant beta (15-30 Hz) oscillatory activity at 25.8±3.7 Hz (mean±SD). The median firing rate (FR) for all STN neurons was 45.5 Hz (25%=27.6, 75%=64.9). Cells with no oscillatory discharge had a median FR of 40.9 Hz (25%=26.5, 75%=61.5), whereas the oscillatory group had a median FR of 52.9 Hz (25%=33.3, 75%=70.65) which was significantly greater (P=0.005, Mann-Whitney Rank Sum test). In 50 (89.3%) of the oscillatory neurons, the activity was coherent with the LFP recorded from one or both electrodes. Neuronal oscillatory activity at other frequencies was only rarely encountered. At all of the sites in STN where LFP activity was recorded from both electrodes, there was significant coherence in the beta range, even in cases fwhere no peak in the beta band was observed in the LFP power spectrum. In contrast, the firing of only 17 of the 67 (25.4%) pairs of cells recorded from the two electrodes was significantly coherent in the beta range. However, coherence was present in 9 of 10 cases where beta oscillations were detected in both cells and in 6 of 15 cases where beta oscillations were detected in just one cell; two pairs were coherent although no beta oscillations were detected in either cell.

Figure 1B:
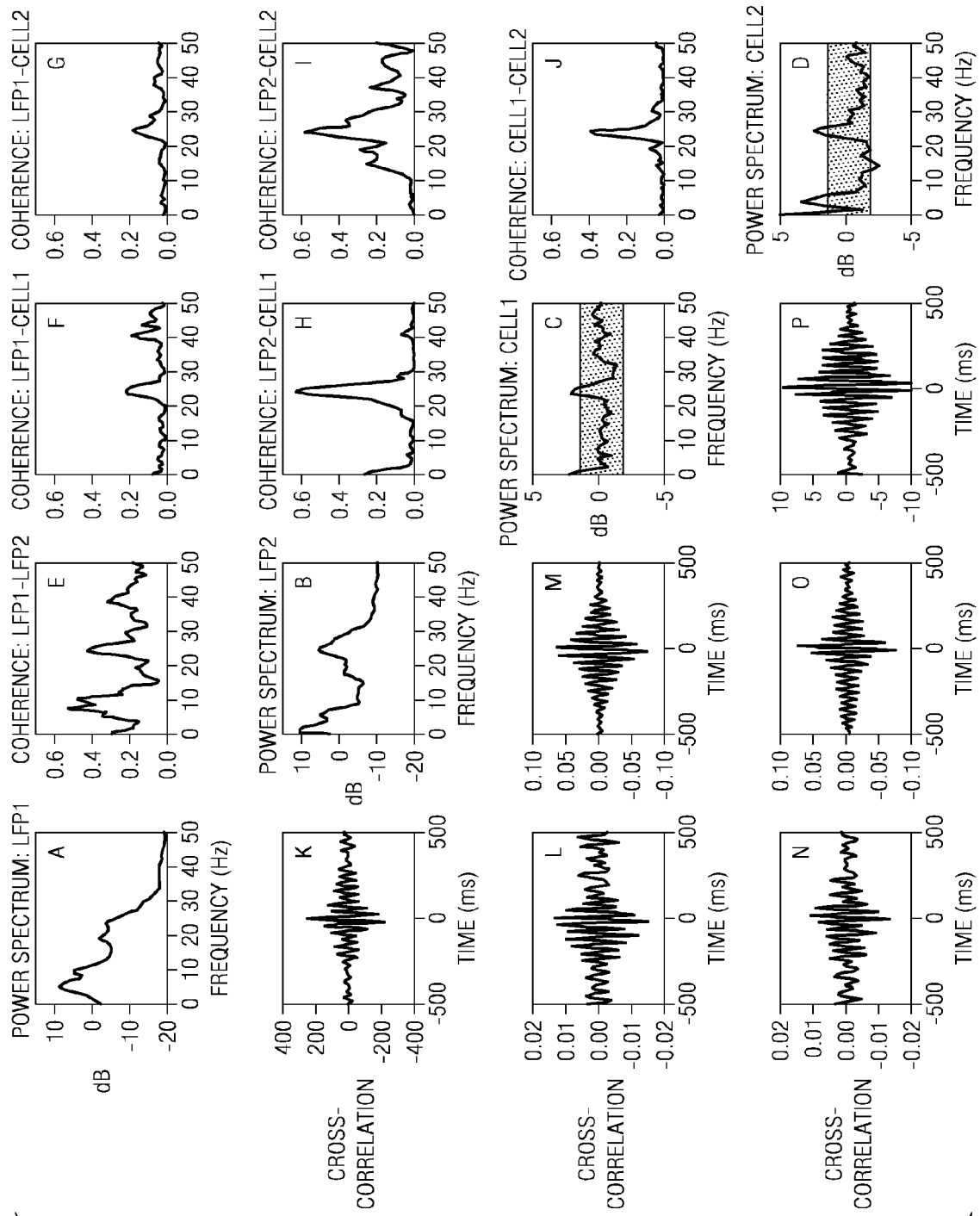

FIGS. 1A and 1B illustrate significant neuronal and LFP beta activity, recorded simultaneously from both microelectrodes (from one patient, right STN), along with their corresponding coherence plots and correlograms.

FIG. 1A shows raw data showing local field potential and multi-unit neuronal discharge recorded simultaneously from the two microelectrodes. Both electrodes were −2.5 mm within the STN.

FIG. 1B shows LFP and neuronal discharge power spectra, obtained from the pair of recording sites, and their corresponding coherence and cross correlation functions. Graphs (a, b) depict LFP power spectra where the dotted line indicates 95% confidence interval of the estimated spectrum. Graphs (c, d) depict neuronal power spectra where the solid and dotted lines indicate the corrected and the actual spectra respectively, shaded area indicates 95% confidence interval for the absence of oscillatory activity. Graphs (e-j) depict coherence functions for each combination where the dotted line indicates 95% confidence limit for the absence of coherence. Graphs (k-p) depict cross-correlograms and spike triggered averages (STA) of the 11-35 Hz band pass filtered LFPs. In graphs (k-p), the dotted line indicates 95% confidence interval for the lack of relationship between the signals.

Incidence of Neuronal Oscillatory Beta Activity is Higher in Dorsal STN

The majority of the beta oscillatory neurons were localized in the dorsal STN. The mean locations(±SEM) of oscillatory (n=56) and non-oscillatory (n=144) cells within the STN were −1.48±0.14 mm and −2.10±0.10 mm respectively (P=0.001, t-test).

Figure 2A:
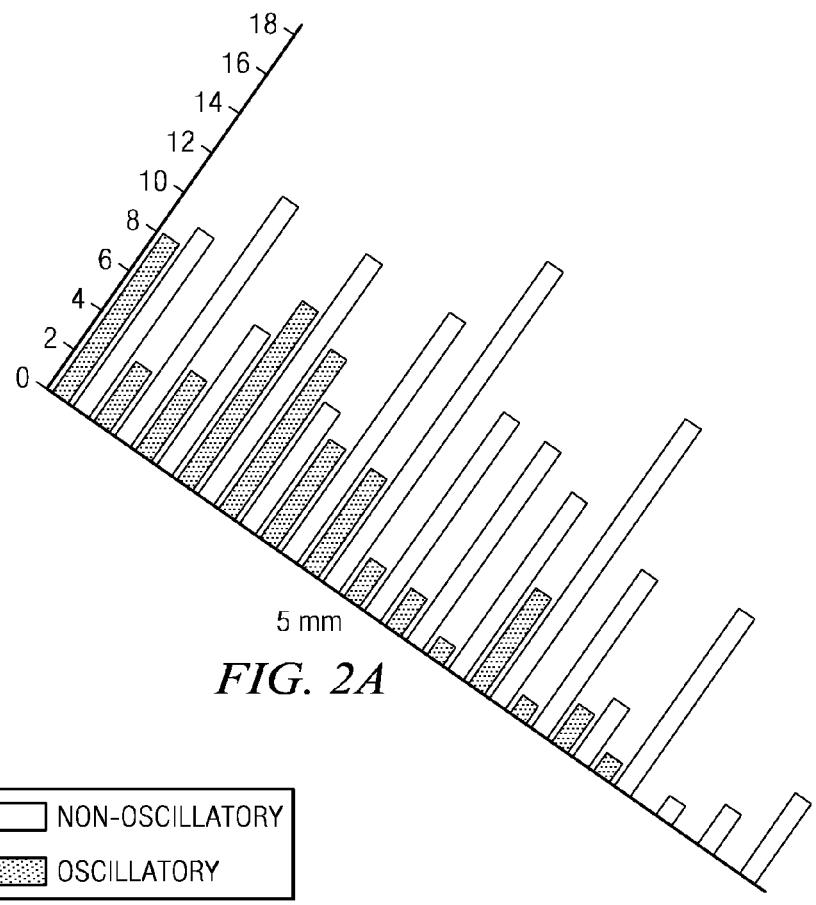
FIGS. 2A and 2B show distribution of the total number of oscillatory and non-oscillatory cells located within the STN as a function of distance within the STN.
Figure 2B:
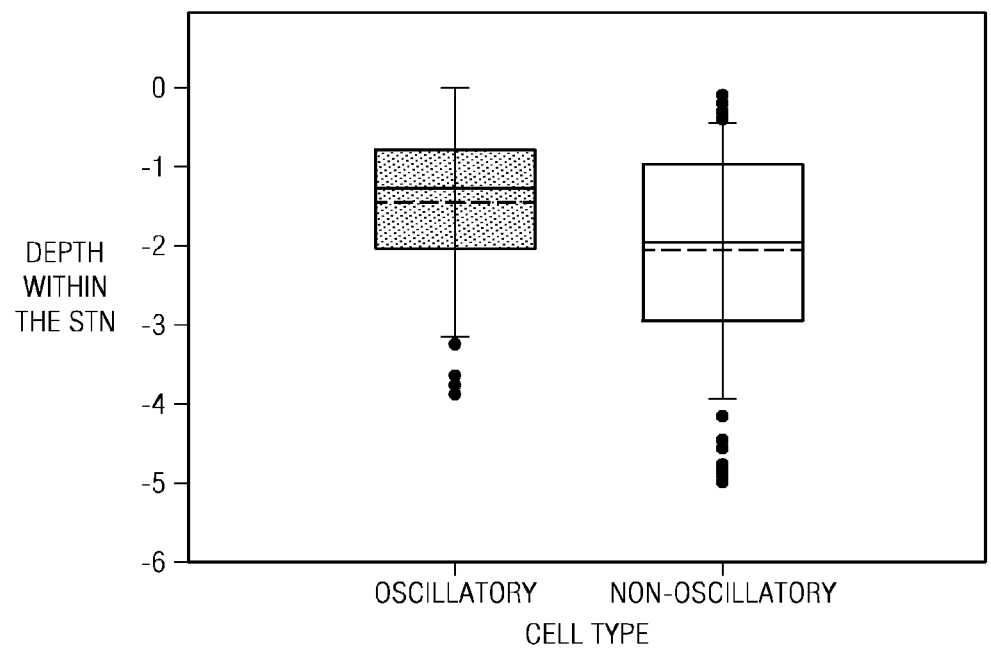

FIGS. 2A and 2B show distribution of the total number of oscillatory and non-oscillatory cells located within the STN. FIG. 2A shows saggital reconstruction of an electrode track showing the total number of oscillatory (n=56) and non-oscillatory (n=144) cells located within the STN from top to bottom (0 to −5 mm respectively) in 0.3 mm intervals.

FIG. 2B shows box plots of oscillatory and non-oscillatory cells' distribution within the STN. Solid and dashed lines indicate the median and the mean depths respectively (mean±SEM: −1.5±0.1 and −2.1±0.1 mm for oscillatory and non-oscillatory cells respectively, P=0.001, t-test).

Of the oscillatory cells, 75% were observed in the dorsal STN while 25% were observed in the ventral STN (n=56, P=0.01). Whereas there was no significant difference in the incidence of non-oscillatory cells in the dorsal and ventral STN (see Table 2). There was a significant relationship between the dorsal/ventral location and the presence/absence of neuronal beta activity (P=0.003, $X^2$ test).

TABLE 2

The percentage of oscillatory and non-oscillatory cells observed within the dorsal (0 to −2 mm) vs. the ventral (−2 to −4 mm) STN.

| | % of cells observed within the dorsal STN | % of cells observed within the ventral STN | Total number of cells |
|---|---|---|---|
| Oscillatory | 75% (n = 42) | 25% (n = 14)* | 56 |
| Non-oscillatory | 54% (n = 74) | 46% (n = 63) | 137 |

LFP Beta Oscillations are Greatest in Dorsal STN

The power of the beta activity recorded from the pair of microelectrodes in the 14 patients was calculated for 351 sites within and immediately above STN. FIGS. 3A-3D depict respective graphs related to LFP beta power from 5 mm dorsal to 5 mm ventral to the dorsal border of STN.

Figure 3A:
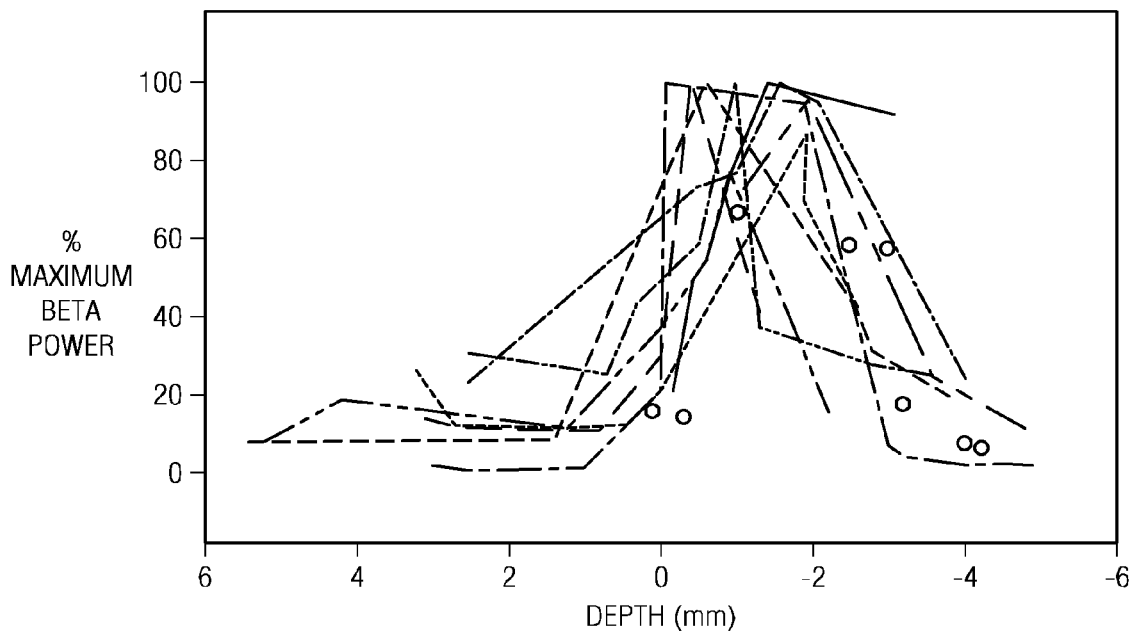
FIGS. 3A-3D depict respective graphs related to LFP beta power distribution from 5 mm above to bottom of STN (−5 mm).

Specifically, FIG. 3A depicts examples of the pattern of variations in the LFP beta power with depth as seen in ten individual patients. Each line represents one microelectrode recording track from one STN side in one patient. Power was expressed as the percentage of the greatest beta LFP power recorded during each track.

Figure 3B:
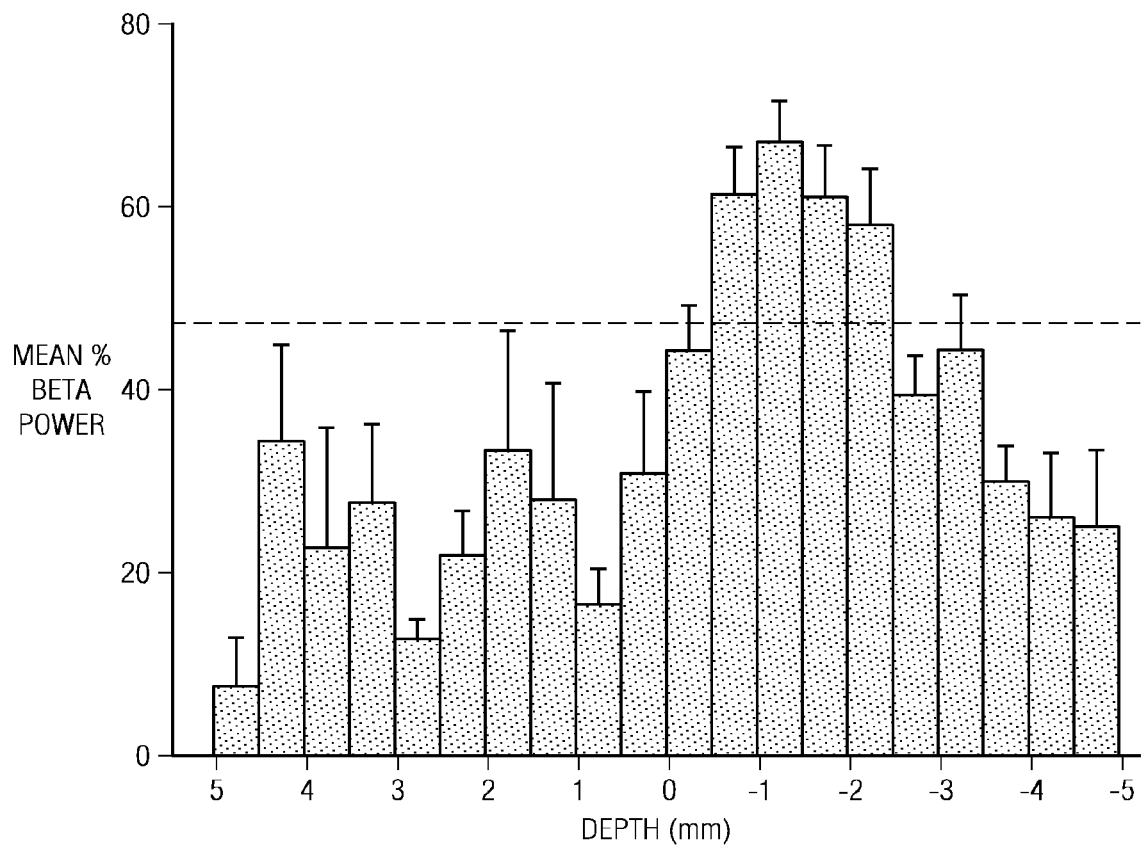
Figure 3C:
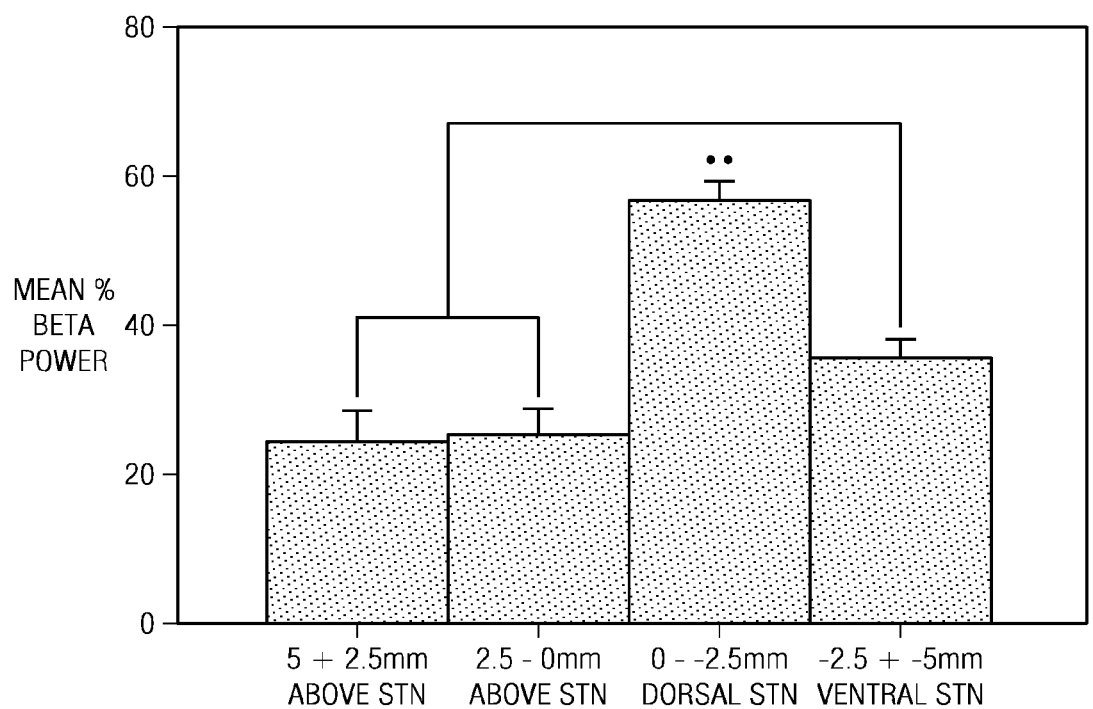

FIG. 3B depicts LFP power averaged across subject (n=14, 21 sides×two electrodes) to give mean percentage maximum beta frequency(±SE) within 0.5 mm intervals. The dashed line indicates the upper 99% confidence limit. As seen in FIG. 3B, averaging the percentage of beta LFP power every 2.5 mm reveals significantly greater power in the dorsal part (0—2.5 mm) of STN (median: 53.8%, 25%=30.7, 75%=87.3) compared to the regions above (5-2.5 and 2.5-0 mm) (medians: 13.3 and 12.5%, 25%=9.0 and 8.7, 75%=24.4 and 38.1 respectively) and below (−2.5—5.0 mm) STN (median: 33.3%, 25%=16.6, 75%=47.3) (P<0.001, Mann-Whitney Rank Sum test) (FIG. 3C). Moreover, the power in the ventral STN was still significantly higher than the power above the STN (P=0.002).

FIG. 3C shows a bar graph that represents the mean percentage LFP power every 2.5 mm. Beta power was seen to increase significantly within the dorsal part compared to above and ventral STN (** P<0.001, Mann-Whitney Rank Sum test). Power was reduced on the ventral part but was still significantly stronger than above STN (*P<0.002). No significant change was observed between the two parts above STN.

Figure 3D:
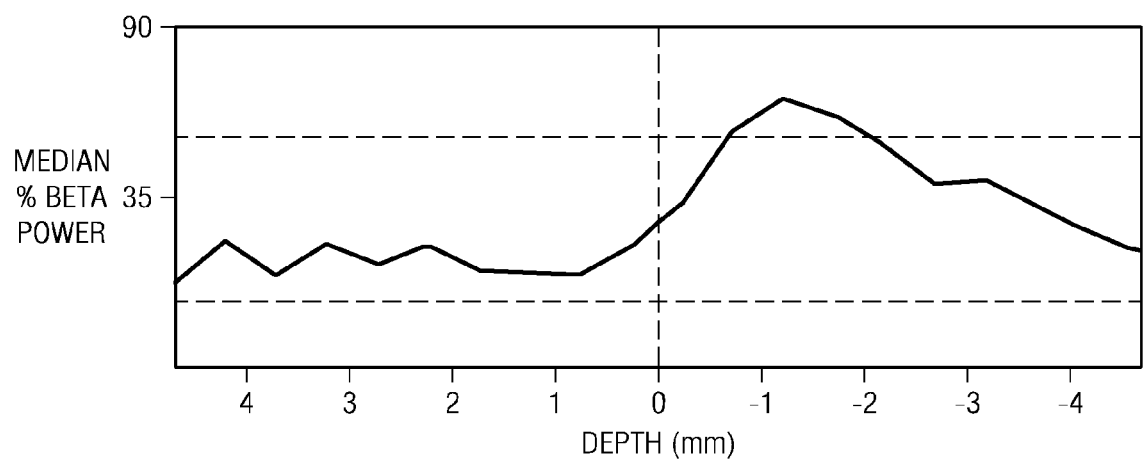

FIG. 3D shows a graphical representation of the results of change-point and control chart analysis which confirm the previously mentioned results. Shifts in the shaded background represent the two changes in the median % LFP beta power according to change-point analysis. First change was increase in LFP power upon the dorsal STN (within −0.5 to −1 mm interval) and the second change was decrease in power within the ventral STN (within −2.5 to −3 mm interval). Dotted lines, indicate 95% control limits, provide an evidence for the significance of both changes. Vertical dashed line represents the top of STN.

Similar analysis of the neuronal oscillatory power revealed a comparable relationship by showing a gradual reduction in the mean beta power from the dorsal to the ventral border of STN. However, change point analysis failed to confirm these changes. When comparing dorsal vs. ventral STN (first and last 2.5 mm), cells in the dorsal STN had a median power of 66.8% (25%=44.7, 75%=97.5), which was significantly higher than the median power in the ventral STN (46.4%, 25%=30.7, 75%=72.3) (P<0.001, Mann-Whitney Rank Sum test). This relationship can result, in part, from the higher incidence of oscillatory cells in the dorsal region. These cells had significantly higher mean(±SEM) of 74.7±3.8% beta power than the mean power of cells with no oscillatory discharge (46.3±2.9%) (P<0.001, t-test). Indeed, when repeating the analysis with taking into account just the non-oscillatory cells, there was no significant difference between the dorsal and the ventral parts of STN.

Neuronal Oscillations Correlate with UPDRS Scores and L-DOPA Response

Figure 4A:
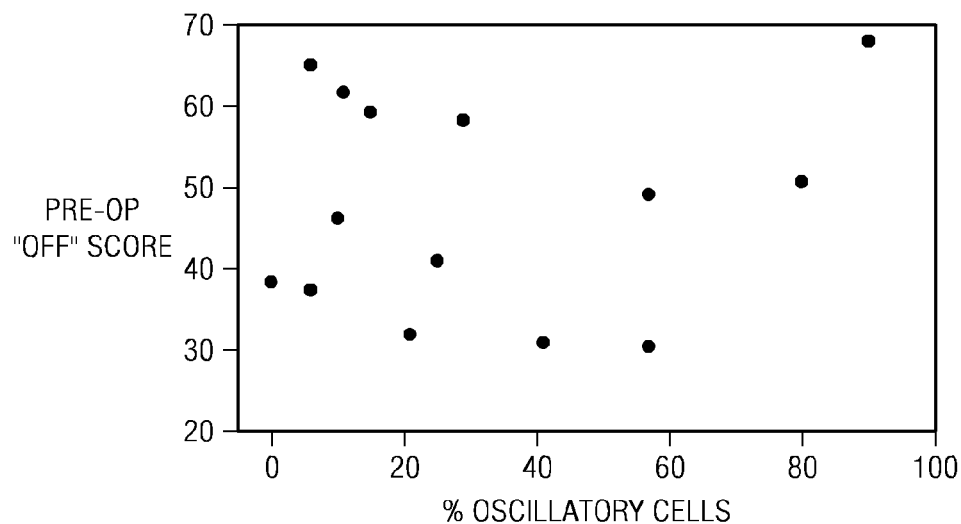
FIGS. 4A-4C show a correlation of the percentage of beta oscillatory cells, observed in each patient, with total motor UPDRS scores and clinical efficacy of L-DOPA medication, assessed pre-operatively (n=14).
Figure 4B:
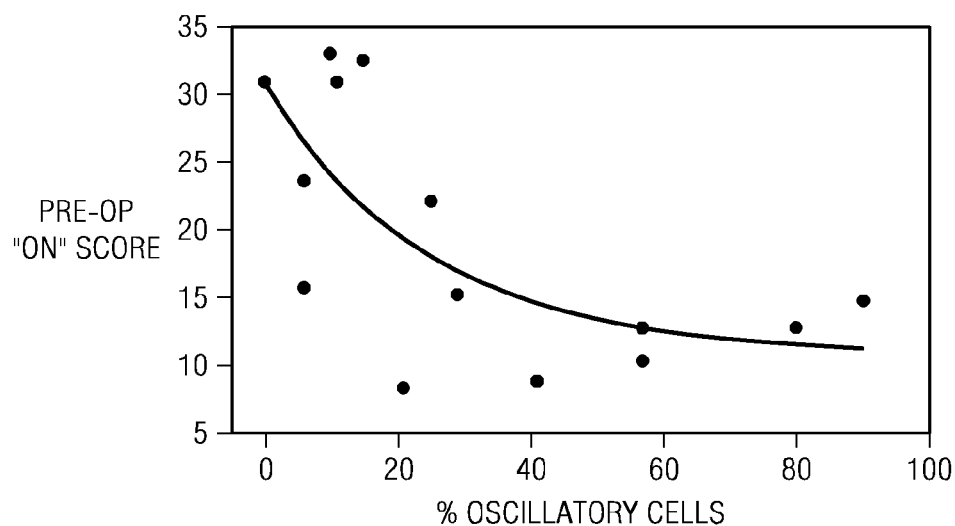
Figure 4C:
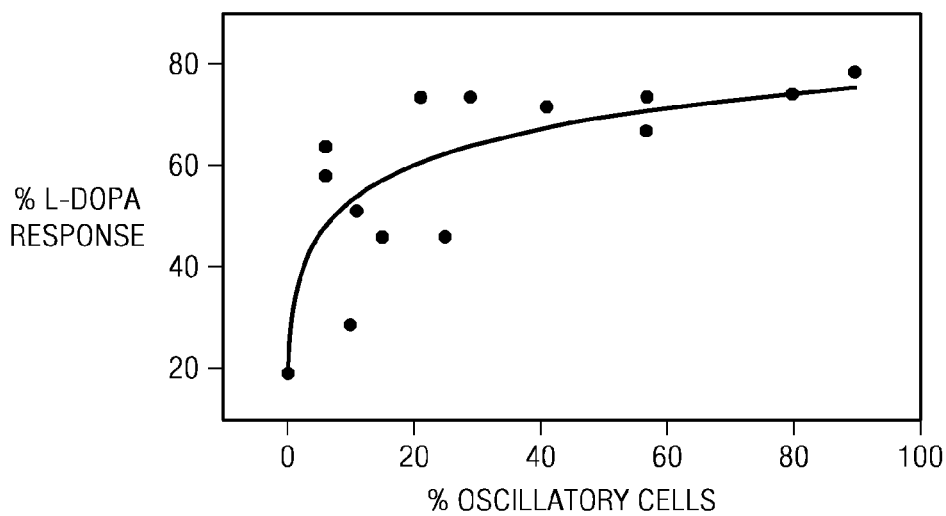

The percentage of beta oscillatory cells in STN (including both sides) was found to vary greatly between patients; however, when the percentage was high on one side, it was also high on the other side. The percentage of beta oscillatory cells was found to be negatively correlated with the "on" drug UPDRS score (FIG. 4B) and positively correlated with the dopaminergic medication response (FIG. 4C) (non-linear regression, R2=0.49, P<0.05 and R2=0.62, P<0.005 respectively). Similar correlation occurred when comparing medication response on tremor and also on the non-tremor sub-scores of the UPDRS. However, no correlation was observed between the percentage of oscillatory cells and "off" drug UPDRS score (FIG. 4A). Moreover, no significant correlations were observed with different UPDRS sub-scores such as tremor, rigidity and posture or with improvement from DBS.

Conclusion

The above clinical data provides evidence on the occurrence of oscillatory activity in both the LFPs and the neuronal firing in the STN. These results demonstrated coherence between neuronal discharge and LFPs in the beta range and also showed that the coherence also occurred for sites separated by 1 or more mms. The Applicants also demonstrated coherence in beta oscillations between LFPs recorded from two microelectrodes separated by a mm or more within STN. These observations suggested that the generators of the beta LFP oscillations were distributed and synchronized over a large region of the STN.

Identifying a Pathological Region of the Brain

Some representative embodiments utilize a technique that can identify regions of the brain, for example pathological regions. The identification technique utilizes the synchronization of neuronal activity that occurs as the result of various brain disorders. Thus, patients are first selected and/or identified based upon physical, chemical and/or historical behavioral data. Once the patient is selected, then electrodes are inserted into the area of interest and neuronal activity is measured. The neuronal signals are analyzed off line or in real-time to determine the synchronization of the neurons, thereby determining a region of the brain that is producing pathological signals. In further embodiments, the technique can be incorporated into a closed loop system providing a feedback that will monitor the effectiveness of the stimulation.

One of skill in the art is aware that pathological signals can include but are not limited to single neuronal activity, rate of discharge, pattern of discharge, interspike interval, bursting index, oscillatory behavior correlated activity in 2 or more neurons that are adjacent or at a distance, local field potentials, EEG changes, magnetoencephalography changes, changes in local pH, ionic concentrations (i.e., potassium), and concentration of neurotransmitters.

Patient Selection

Subjects to be treated according to some representative embodiments can be selected, identified and/or diagnosed based upon the accumulation of physical, chemical, and historical behavioral data on each patient. One of skill in the art is able to perform the appropriate examinations to accumulate such data. One type of examination can include neurological examinations, which can include mental status evaluations, which can further include a psychiatric assessment. Other types of assessments for movement disorders may include such assessments for example using the Unified Parkinson's Disease Rating Scale (UPDRS). Still further, other types of examinations can include, but are not limited to, motor examination, cranial nerve examination, cognitive assessment and neuropsychological tests (i.e., Minnesota Multiphasic Personality Inventory, Beck Depression Inventory, or Hamilton Rating Scale for Depression). In addition to neurological testing, routine hematological and/or biochemistry testing may also be performed.

In addition to the above examinations, imaging techniques can be used to determine normal and abnormal brain function that can result in disorders. Thus, once the patient is identified from the above clinical examinations, imaging techniques can be further utilized to provide the region of interest in which the electrodes are to be implanted. Functional brain imaging allows for localization of specific normal and abnormal functioning of the nervous system. This includes electrical methods such as electroencephalography (EEG), magnetoencephalography (MEG), single photon emission computed tomography (SPECT), as well as metabolic and blood flow studies such as functional magnetic resonance imaging (fMRI), and positron emission tomography (PET) which can be utilized to localize brain function and dysfunction.

A. Examination of Neuronal Signals

Once a patient is identified, then some representative embodiments are utilized to determine a specific location within the brain that exhibits pathological neuronal activity. Identification of a brain region that has pathological neuronal activity may utilize standard implanted electrodes to measure and/or record neuronal activity, for example neuronal activity and/or local field potentials. Neuronal activity that is considered to be pathological in the present invention may comprise neuronal discharge activity and/or local field potentials (LFPs) in the beta range (15-30 Hz). Furthermore, the neuronal discharge and/or LFPs may also be considered oscillatory activity in the beta range. More preferably, the pathological activity may also be represented by a coherence or synchronization of the neuronal discharges and LFPs in the beta range.

While not being bound by the description of a particular procedure, patients who are to have an electrical stimulation lead or electrode implanted into the brain, generally, first have a stereotactic head frame, such as the Leksell, CRW, or Compass, mounted to the patient's skull by fixed screws. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images or functional imaging (PET or SPECTscan, fMRI, MSI), or indirectly using interactive anatomical atlas programs that map the atlas image onto the stereotactic image of the brain. As is described in greater detail elsewhere in this application, the anatomical targets or predetermined site may be stimulated directly or affected through stimulation in another region of the brain.

In preferred embodiments, the site or implant sites include, but are not limited to thalamus/sub-thalamus, basal ganglia, globus pallidus, cortex or white matter tracts afferent to or efferent from the abovementioned brain tissue. More specifically, the site associated with the subthalamic nucleus (STN) includes the dorsal STN and the dorsolateral STN.

By selecting appropriate stimulation sites, representative embodiments enable modulation of neuronal activity to affect the motor system to treat movement disorders. Representative embodiments find particular application in the modulation of neuronal function or processing to effect a functional outcome. The modulation of neuronal function is particularly useful with regard to the prevention, treatment, or amelioration of movement, psychiatric, psychological, conscious state, behavioral, mood, mental activity, cognitive ability, memory and thought activity.

Figure 5:
FIG. 5 depicts a stimulation lead that may be employed for implantation within a patient.
Figure 6:
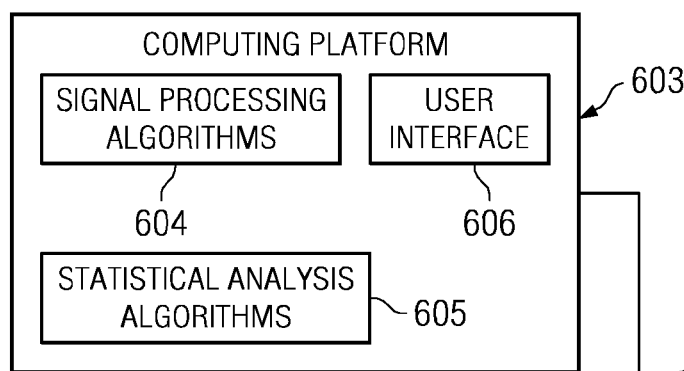
FIG. 6 depicts a system to identify a region within the brain according to one representative embodiment.

Upon implanting a stimulation lead 501, as shown in FIG. 5, with electrodes disposed near, adjacent to, or within the target brain tissue, some representative embodiments utilize the detection and analysis of neuronal spike discharge activity and LFP activity to confirm that the electrodes are properly positioned. Specifically, terminals of the stimulation lead may be coupled using respective conductors 601 to suitable electronic circuitry 602 to enable measurement of the neuronal spike discharge activity and LFP activity as shown in FIG. 6. Suitable electronic equipment for initial signal sampling and processing include the Guideline System 3000 available from Axon Instruments and the CED 1401 device available from Cambridge Electronic Designs. Further signal processing may occur on a suitable computer platform 603 using available signal processing and statistical analysis libraries (e.g., MATLAB). The computer platform may include suitable signal processing algorithms 604 (e.g., time domain segmentation, FFT processing, windowing, logarithmic transforms, etc.). Statistical processing may be applied by statistical analysis algorithms 605. User interface software 606 may be used to present the processed neuronal spike data, the LPF data, and the results of the correlation analysis using a suitable user interface. If neuronal spike discharge activity and LFP activity are determined to be correlated after processing by algorithms 605, the current position of the electrodes is confirmed as the proper location for subsequent delivery of stimulation pulses to treat the neurological disorder. The location of the electrodes can then be fixed using suitable burr hole cap functionality as an example. If such neuronal spike activity and LFP activity are not correlated, further adjustment of the electrode position may occur.

Figure 7:
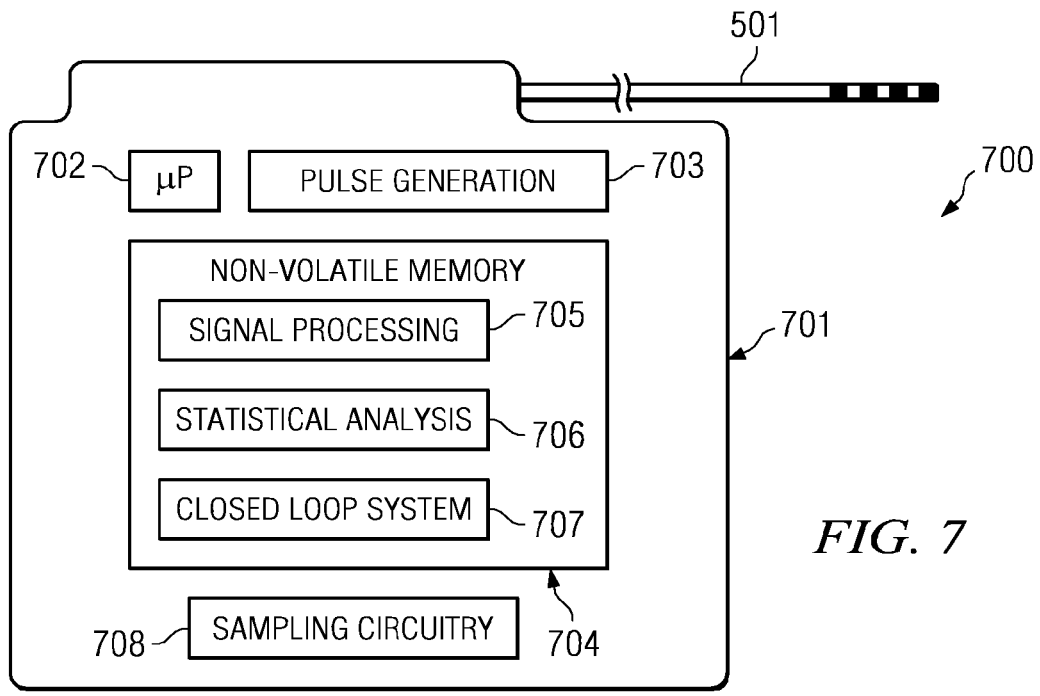
FIG. 7 depicts a stimulation system according to one representative embodiment.

In other representative embodiments, the sampling and processing of the signals representative of the neuronal discharge and LFP is performed by an implantable pulse generator (IPG). One of skill in the art is aware that commercially available implantable pulse generators can be modified to implement representative embodiments. That is, one of skill in the art would be able to modify an existing IPG to achieve the desired results. An exemplary IPG that is commercially available is the EON® pulse generator (manufactured by Advanced Neuromodulation Systems, Inc.). FIG. 7 depicts IPG 700 adapted according to one representative embodiment. As shown in FIG. 7, IPG 700 comprises processor 702 that possesses sufficient computational capacity to perform the respective digital signal processing and statistical analysis algorithms. The digital signal processing and statistical analysis is preferably performed by software code stored in memory 704 of the IPG (shown as signal processing code 705 and statistical analysis code 706). Closed-loop system code 707 preferably employs the data from code 705 and code 706 to control pulse generation circuitry 703. Additionally, IPG 700 preferably comprises circuitry 708 to facilitate the sampling of the neuronal signals such as an analog-to-digital (AD) converter, amplification circuitry, and/or filtering circuitry.

Moreover, sensors that can be used in the present invention can include, for example, epicordical leads, deep brain leads, or peripheral leads. Examples of leads that could be used include, a single multi electrode lead with four electrodes each having a width of 2 mm with adjacent electrodes being separated by 2½ mm (as shown as lead 501 in FIG. 5). Another example is a lead with two 1 cm electrodes with a 2 mm intervening gap. Yet further, another example is a 2 or 3 branched lead/catheter to cover the predetermined site or target site. Each one of the prongs may include four electrodes of 1-2 mm width with a center to center separation of 2 of 2.5 mm and a span of 1.5 mm.

In embodiments where beta-oscillation detection and analysis is implemented in an IPG, the stimulation functionality of the IPG is preferably controlled in a closed loop or open loop manner in response to detection of beta oscillatory synchronization. In some embodiments, measurements of neuronal spike activity and LFP activity are made utilizing suitable electrodes of a stimulation lead. The neuronal spike activity and LPF activity are processed to identify activity within the beta band. If beta activity is detected, suitable signal processing is performed to determine the correlation or synchronization between the neuronal spike beta activity and the LFP beta activity. If sufficient correlation or synchronization is found, stimulation pulses are generated and delivered to the target region of the brain (e.g., the dorsal portion of the STN) using one or more electrodes. In certain embodiments, another related site that would indirectly alter the pathological neuronal activity may be stimulated. Additionally, the pulse amplitude, pulse width, and pulse frequency may be modified depending upon the detection of correlation or synchronization in such beta activity. For example, if stimulation for a predetermined period of time does not reduce or modify the synchronized beta activity, a control loop (as implemented by software instructions of the IPG) may increase the amplitude or increase the pulse width of the stimulation pulses applied to the target region. When the suppression of the pathological neuronal activity is detected, the electrical stimulation may temporarily cease or the stimulation amplitude or pulse width may be reduced.

The types of stimulation used for the treatment of the pathological findings are known to those of skill in the art. The electrical stimulation can, for example, be long periodic sequences of discrete electrical stimulation pulses or electrical stimulation sequences or patterns. As a consequence of the electrical stimulation used, longer periodic sequences of discrete electrical stimulation pulses typically suppress the pathological activity while electrical stimulation patterns typically bring the activity closer to the natural nonpathologically activity or cause the activity to completely resume the normal nonpathological activity. Any stimulation methodology that is effective in mitigating, reducing, or eliminating the exhibited pathological neuronal activity may be employed by representative embodiments.

Although some representative embodiments have been described in terms of a single integrated device for implantation within a patient, other designs may be employed. For example, an external controller may wirelessly communicate (e.g., using RF communications) with an implantable pulse generator. The wireless communications may communicate the data detected by the sensors of the implanted device and the external controller may process the communicated data. In response to detection of pathological neuronal activity, the external controller may signal the implanted pulse generator to begin stimulating the target neuronal tissue that is exhibiting the pathological activity. Additionally, wireless communication of the neuronal data may be utilized to determine whether the stimulation therapy is effective or whether selected stimulation parameters are no longer optimal.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example system into a person for sensing neuronal activity, and in certain embodiments, sensing pathological neuronal activity and stimulating to reduce, abrogate, override or alter the pathological activity such that it resembles or is similar to nonpathological activity.

Using representative embodiments, a target area is stimulated either directly or indirectly in an effective amount or effective treatment regimen to decrease, reduce, modulate or abrogate movement disorders. Thus, a subject is administered a therapeutically effective stimulation so that the subject has an improvement in the parameters relating to the movement disorder including subjective measures such as, for example, Unified Parkinson's Disease Rating Scale (UPDRS), other neurological examinations and neuropsychological tests (i.e., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, other alterations in cerebral blood flow or metabolism and/or neurochemistry, or nerve conduction studies. The improvement is any observable or measurable improvement. Thus, one of skill in the art realizes that a treatment may improve the patient condition, but may not be a complete cure of the disease.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

According to one embodiment of the present invention, the identified target site is stimulated using stimulation parameters such as, pulse width of about 1 to about 500 microseconds, more preferably, about 1 to about 90 microseconds; frequency of about 1 to about 300 Hz, more preferably, about 100 to about 185 Hz; and voltage of about 0.5 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether objective or subjective.

Movement disorders that may be treated using the present invention can include, but are not limited to restless leg syndrome, dyskinesia (e.g., tremor, dystonia, chorea and ballism, tic syndromes (e.g., Tourette's Syndrome), myoclonus, drug-induced movement disorders, Wilson's Disease, Paroxysmal Dyskinesias, Stiff Man Syndrome, Akinetic-Ridgid Syndromes and Parkinsonism, ataxic disorders (e.g., disturbances of gait). More specifially, the movement disorder may include akinesia (lack of movement), athetosis (contorted torsion or twisting), ataxia ballismus (violent involuntary rapid and irregular movements), hemiballismus bradykinesia (slow movement), chorea (rapid, involuntary movement), Sydenham's chorea, Rheumatic chorea, Huntington's chorea, Dystonia (sustained torsion), Dystonia muscularum, Blepharospasm, Writer's cramp, Spasmodic torticollis (twisting of head and neck), and Parkinson's disease.

In more specific aspects of the present invention, the methods may be used to treat or improve at least one symptom associated with Parkinson's disease. Symptoms of Parkinson's disease may include the primary and/or secondary symptoms. Primary symptoms may include bradykinesia, tremors, rigidity, poor balance, and Parkinson's Gait. Secondary symptoms may include, but are not limited to constipation, difficulty swallowing, excessive salivation, excessive sweating, loss of bowel and/or bladder control, mental impairment, anxiety, depression, etc.

In addition to electrical stimulation being used to treat the movement disorder, it may be desirable to use a drug delivery system independently or in combination with electrical stimulation to result in the stimulation parameters of the present invention. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any type of infusion pump can be used in the present invention. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 all of which are incorporated by reference in their entirety. Pumps of this type are commercially available, for example, Model 3000® from Arrow International, Reading, Penn. and IsoMed® from Medtronic, Inc., Minneapolis, Minn.; AccuRx® pump from Advanced Neuromodulation Systems, Inc., Plano, Tex.

In certain embodiments, the catheter can be in the form of a lead catheter combination, similar to the ones described in U.S. Pat. No. 6,176,242 and U.S. Pat. No. 5,423,877, which are incorporated herein by reference in their entirety.

Still further, the present invention can comprise a chemical stimulation system that comprises a system to control release of neurotransmitters (e.g., glutamate, acetylcholine, norepinephrine, epinephrine, dopamine), chemicals (e.g., zinc, magnesium, lithium) and/or pharmaceuticals that are known to alter the activity of neuronal tissue. For example, infusion formulation delivery system can utilize a control system having an input-response relationship. A sensor generates a sensor signal representative of a system parameter input (such as levels of neurotransmitters), and provides the sensor signal to a controller. The controller receives the sensor signal and generates commands that are communicated to the infusion formulation delivery device. The infusion formulation delivery device then delivers the infusion formulation output to the predetermined site at a determined rate and amount in order to control the system parameter.

Sensor may comprise a sensor, sensor electrical components for providing power to the sensor and generating the sensor signal, a sensor communication system for carrying the sensor signal to controller, and a sensor housing for enclosing the electrical components and the communication system. Controller may include one or more programmable processors, logic circuits, or other hardware, firmware or software components configured for implementing the control functions described herein, a controller communication system for receiving the sensor signal from the sensor, and a controller housing for enclosing the controller communication system and the one or more programmable processors, logic circuits, or other hardware, firmware or software components. The infusion formulation delivery device may include a suitable infusion pump, infusion pump electrical components for powering and activating the infusion pump, an infusion pump communication system for receiving commands from the controller, and an infusion pump housing for enclosing the infusion pump, infusion pump electrical components, and infusion pump communication system. Such systems are described in U.S. Pat. No. 6,740,072, which is incorporated herein by reference in its entirety.

In certain embodiments, the sensor can be an electrode that senses a hyperactive burst pattern of activity, which in turns stimulates the infusion pump to release a chemical or stimulating drug or agent to modify the neuronal activity. The chemical or stimulating agent can be either an inhibiting agent or stimulating agent.

Herein, stimulating drugs comprise medications, anesthetic agents, synthetic or natural peptides or hormones, neurotransmitters, cytokines and other intracellular and intercellular chemical signals and messengers, other agents such as zinc and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts, anesthetics (e.g., lidocane), and magnesium may also be used in combination with electrical stimulation.

In addition to electrical stimulation and/or chemical stimulation, other forms of stimulation can be used, for example magnetic, or thermal or combinations thereof. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Thermal stimulation can be provided by using implanted probes that are regulated for heat and/or cold temperatures which can stimulate or inhibit neuronal activity, for example, U.S. Pat. No. 6,567,696, which is incorporated herein by reference in its entirety.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Bergman H, Wichmann T, Karmon B, DeLong M R (1994) The primate subthalamic nucleus. II. Neuronal activity in the MPTP model of parkinsonism. J Neurophysiol 72:507-520.

Bevan M D, Magill P J, Terman D, Bolam J P, Wilson O (2002) Move to the rhythm: oscillations in the subthalamic nucleus-external globus pallidus network. Trends Neurosci 25:525-531.

Brown P, Oliviero A, Mazzone P, Insola A, Tonali P, Di L, V (2001) Dopamine dependency of oscillations between subthalamic nucleus and pallidum in Parkinson's disease. J Neurosci 21:1033-1038.

Cassidy M, Mazzone P, Oliviero A, Insola A, Tonali P, Di L, V, Brown P (2002) Movement-related changes in synchronization in the human basal ganglia. Brain 125:1235-1246.

DeLong M R, Crutcher M D, Georgopoulos A P (1985) Primate globus pallidus and subthalamic nucleus: functional organization. J Neurophysiol 53:530-543.

Doyle L M, Kuhn A A, Hariz M, Kupsch A, Schneider G H, Brown P (2005) Levodopa-induced modulation of subthalamic beta oscillations during self-paced movements in patients with Parkinson's disease. Eur J Neurosci 21:1403-1412.

Filali M, Hutchison W D, Palter V N, Lozano A M, Dostrovsky J O (2004) Stimulation-induced inhibition of neuronal firing in human subthalamic nucleus. Exp Brain Res 156:274-281.

Filion M, Tremblay L (1991) Abnormal spontaneous activity of globus pallidus neurons in monkeys with MPTP-induced parkinsonism. Brain Res 547:142-151.

Fogelson N, Williams D, Tijssen M, van B G, Speelman H, Brown P (2006) Different Functional Loops between Cerebral Cortex and the Subthalmic Area in Parkinson's Disease. Cereb Cortex 16:64-75.

Halliday D M, Rosenberg J R, Amjad A M, Breeze P, Conway B A, Farmer S F (1995) A framework for the analysis of mixed time series/point process data—theory and application to the study of physiological tremor, single motor unit discharges and electromyograms. Prog Biophys Mol Biol 64:237-278.

Hutchison W D, Allan R J, Opitz H, Levy R, Dostrovsky J O, Lang A E, Lozano A M (1998) Neurophysiological identification of the subthalamic nucleus in surgery for Parkinson's disease. Ann Neurol 44:622-628.

Jahanshahi M, Ardouin C M, Brown R G, Rothwell J C, Obeso J, Albanese A, Rodriguez-Oroz M C, Moro E, Benabid A L, Pollak P, Limousin-Dowsey P (2000) The impact of deep brain stimulation on executive function in Parkinson's disease. Brain 123 (Pt 6):1142-1154.

Kuhn A A, Trottenberg T, Kivi A, Kupsch A, Schneider G H, Brown P (2005) The relationship between local field potential and neuronal discharge in the subthalamic nucleus of patients with Parkinson's disease. Exp Neurol 194:212-220.

Kuhn A A, Williams D, Kupsch A, Limousin P, Hariz M, Schneider G H, Yarrow K, Brown P (2004) Event-related beta desynchronization in human subthalamic nucleus correlates with motor performance. Brain 127:735-746.

Levy R, Ashby P, Hutchison W D, Lang A E, Lozano A M, Dostrovsky J O (2002) Dependence of subthalamic nucleus oscillations on movement and dopamine in Parkinson's disease. Brain 125:1196-1209.

Levy R, Hutchison W D, Lozano A M, Dostrovsky J O (2000) High-frequency synchronization of neuronal activity in the subthalamic nucleus of parkinsonian patients with limb tremor. J Neurosci 20:7766-7775.

Lozano A M, Dostrovsky J, Chen R, Ashby P (2002) Deep brain stimulation for Parkinson's disease: disrupting the disruption. Lancet Neurol 1:225-231.

Magill P J, Bolam J P, Bevan M D (2001) Dopamine regulates the impact of the cerebral cortex on the subthalamic nucleus-globus pallidus network. Neuroscience 106:313-330.

Magill P J, Sharott A, Bevan M D, Brown P, Bolam J P (2004) Synchronous unit activity and local field potentials evoked in the subthalamic nucleus by cortical stimulation. J Neurophysiol 92:700-714.

Marsden J F, Limousin-Dowsey P, Ashby P, Pollak P, Brown P (2001) Subthalamic nucleus, sensorimotor cortex and muscle interrelationships in Parkinson's disease. Brain 124:378-388.

Maurice N, Deniau J M, Menetrey A, Glowinski J, Thierry A M (1998) Prefrontal cortex-basal ganglia circuits in the rat: involvement of ventral pallidum and subthalamic nucleus. Synapse 29:363-370.

Monakow K H, Akert K, Kunzle H (1978) Projections of the precentral motor cortex and other cortical areas of the frontal lobe to the subthalamic nucleus in the monkey. Exp Brain Res 33:395-403.

Nambu A, Takada M, Inase M, Tokuno H (1996) Dual somatotopical representations in the primate subthalamic nucleus: evidence for ordered but reversed body-map transformations from the primary motor cortex and the supplementary motor area. J Neurosci 16:2671-2683.

Nini A, Feingold A, Slovin H, Bergman H (1995) Neurons in the globus pallidus do not show correlated activity in the normal monkey, but phase-locked oscillations appear in the MPTP model of parkinsonism. J Neurophysiol 74:1800-1805.

Parent A, Hazrati L N (1995) Functional anatomy of the basal ganglia. II. The place of subthalamic nucleus and external pallidum in basal ganglia circuitry. Brain Res Brain Res Rev 20:128-154.

Priori A, Foffani G, Pesenti A, Bianchi A, Chiesa V, Baselli G, Caputo E, Tamma F, Rampini P, Egidi M, Locatelli M, Barbieri S, Scarlato G (2002) Movement-related modulation of neural activity in human basal ganglia and its L-DOPA dependency: recordings from deep brain stimulation electrodes in patients with Parkinson's disease. Neurol Sci 23 Suppl 2:S101-S102.

Rodriguez-Oroz M C, Rodriguez M, Guridi J, Mewes K, Chockkman V, Vitek J, DeLong M R, Obeso J A (2001) The subthalamic nucleus in Parkinson's disease: somatotopic organization and physiological characteristics. Brain 124:1777-1790.

Rosenberg J R, Amjad A M, Breeze P, Brillinger D R, Halliday D M (1989) The Fourier approach to the identification of functional coupling between neuronal spike trains. Prog Biophys Mol Biol 53:1-31.

Sharott A, Magill P J, Harnack D, Kupsch A, Meissner W, Brown P (2005) Dopamine depletion increases the power and coherence of beta-oscillations in the cerebral cortex and subthalamic nucleus of the awake rat. Eur J Neurosci 21:1413-1422.

Sterio D, Beric A, Dogali M, Fazzini E, Alfaro G, Devinsky O (1994) Neurophysiological properties of pallidal neurons in Parkinson's disease. Ann Neurol 35:586-591.

Taylor W A (2000) Change-point analysis: a powerful new tool for detecting changes.

Williams D, Kuhn A, Kupsch A, Tijssen M, van B G, Speelman H, Hotton G, Yarrow K, Brown P (2003) Behavioural cues are associated with modulations of synchronous oscillations in the human subthalamic nucleus. Brain 126:1975-1985.

Williams D, Tijssen M, van B G, Bosch A, Insola A, Di L, V, Mazzone P, Oliviero A, Quartarone A, Speelman H, Brown P (2002) Dopamine-dependent changes in the functional connectivity between basal ganglia and cerebral cortex in humans. Brain 125:1558-1569.

Wingeier B, Tcheng T, Koop M M, Hill B C, Heit G, Bronte-Stewart H M (2005) Intra-operative STN DBS attenuates the prominent beta rhythm in the STN in Parkinson's disease. Exp Neurol.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed:

1. A method of identifying a region of the brain comprising the steps of:
    measuring neuronal firing and local field potential by recording electrical signals in the brain using at least a first electrode and a second electrode;
    detecting neuronal spiking activity that is oscillatory within a beta frequency band between 15 Hz and 30 Hz using at least the first electrode, wherein the detecting comprises determining a peak frequency within the beta frequency band range having a largest power spectrum peak and determining a power value within a predetermined frequency range about the peak frequency to represent beta oscillatory activity of the patient;
    comparing occurrence of the detected neuronal spiking activity with activity within the beta frequency band of the local field potential measured by at least the second electrode;
    determining counts of neurons exhibiting neuronal spiking activity occurring within the beta frequency band in relation to movement of the first electrode along an electrode track; and
    analyzing the counts of neurons exhibiting neuronal spiking activity along the electrode track to distinguish between a dorsal portion of the subthalamic nucleus and a ventral portion of subthalamic nucleus to identify the region of the brain.

2. The method of claim 1, wherein the comparing includes detecting whether neuronal spiking activity and the measured local field potential are synchronized.

3. The method of claim 1 further comprising the step of stimulating the identified brain region to disrupt the discharges thereby treating a disease.

4. The method of claim 3, wherein the disease is a movement disorder.

5. The method of claim 4, wherein the movement disorder is Parkinson's disease.

6. The method of claim 1 further comprising:
    detecting synchronized spiking activity in two respective neurons.

7. The method of claim 1 wherein the comparing further comprising:
    calculating a coherence metric between neuronal spiking activity with activity within the beta frequency band of the local field potential while the first electrode and the second electrode are separated by at least 1 mm.

8. The method of claim 1 further comprising:
    calculating a first power metric for activity within the dorsal portion of the subthalamic nucleus; and
    calculating a second power metric for activity within the ventral portion of the subthalamic nucleus.

9. The method of claim 1 further comprising:
    determining a frequency of peak power for activity within the beta frequency band of the local field potential.

* * * * *